US00PP12547P2

(12) United States Plant Patent
Lamb

(10) Patent No.: US PP12,547 P2
(45) Date of Patent: Apr. 16, 2002

(54) SPATHIPHYLLUM PLANT NAMED 'CLAUDIA'

(75) Inventor: Ann E. Lamb, Sebring, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/656,224

(22) Filed: Sep. 6, 2000

(51) Int. Cl.[7] ..... A01H 5/00

(52) U.S. Cl. ..... Plt./364

(58) Field of Search ..... Plt./364

(56) References Cited

U.S. PATENT DOCUMENTS

PP10,893 P * 5/1999 Strode ..... Plt./364

* cited by examiner

*Primary Examiner*—Bruce R. Campell
*Assistant Examiner*—Annette H. Para
(74) *Attorney, Agent, or Firm*—Foley & Lardner

(57) ABSTRACT

A new Spathiphyllum plant named 'Claudia' characterized by its intermediate, upright stature, shiny, dark green textured foliage and elliptic, white spathes. Plants of Claudia are adaptable to pot sizes from 15 cm through 20 cm. Plants of 'Claudia' grow quickly to marketable size and are relatively tolerant of adverse growing conditions and common soil borne pathogens. The new cultivar is particularly well adapted to, and is durable in indoor/interior scape conditions.

4 Drawing Sheets

BACKGROUND OF THE INVENTION

The present invention comprises a new and distinct cultivar of Spathiphyllum, botanically known as Spathiphyllum hybrid, and hereinafter referred to by the cultivar name, 'Claudia.'

The new cultivar is the product of a breeding program carried out by the inventor Ann E. Lamb. The new cultivar named 'Claudia' is a result of a cross made in Apopka, Fla. in October of 1996. The female or seed parent is the cultivar Spathiphyllum 'Sparkle' (U.S. Plant Pat. No. 8,367). The male or pollen parent is Spathiphyllum '31581' (U.S. Plant Pat. No. 10,893).

The new cultivar named 'Claudia' was discovered and selected by the inventor from a group of seedlings of the stated cross in Apopka, Fla. on Mar. 20, 1998. Propagation by tissue culture in the laboratories of Twyford Plant Laboratories, Inc., in Sebring, Fla., under the supervision of the inventor, was used to increase the number of plants for evaluation and has demonstrated the stability of the combination of characteristics as herein described from generation to generation, are firmly fixed and reproduces true to type.

BRIEF DESCRIPTION OF THE DRAWINGS

The accompanying color photographic illustrations show typical characteristics of a 10-month-old plant of 'Claudia' grown in a 15 cm pot initiated from three microcuttings obtained by tissue culture and grown under appropriate growing conditions, with colors being as nearly true as possible with illustrations of this type.

Sheet 1 is a side view showing the inflorescence and foliage of a plant of 'Claudia.'

Sheet 2 is a close-up view of the inflorescence of the instant plant.

Sheet 3 shows the details of the upper leaf surface.

Sheet 4 shows the details of the lower leaf surface.

DETAILED DESCRIPTION OF THE NEW VARIETY

The following traits have been repeatedly observed and are determined to be basic characteristics of 'Claudia' which in combination distinguish this Spathiphyllum as a new and distinct cultivar:

1. Plants are of intermediate stature, and upright habit, and are ideally suited for 15 cm pots. However, the variety may be finished in pots 20 cm and larger.
2. Leaves of 'Claudia' are dark green, with a shiny textured surface.
3. Plants of 'Claudia' grow to marketable size quickly.
4. The spathes of 'Claudia' are pure white, narrow and elliptic in shape, and are held above the foliage.
5. Plants of 'Claudia' are relatively tolerant of adverse growing conditions and common soil borne pathogens.
7. Plants of 'Claudia' are particularly well adapted to, and durable in indoor/interior scape conditions.

'Claudia' has not been observed under all possible environmental conditions. The phenotype of the new cultivar may vary significantly with variations in environment such as temperature, light intensity, and daylength, without however, any change in genotype.

Of the commercial cultivars known to the present inventor, the most similar in comparison to 'Claudia' is the well known commercial cultivar named 'Petite' (unpatented). In comparison to 'Petite', however, 'Claudia' has a taller growth habit and larger, wider, textured leaves. Plants of 'Claudia' are more tolerant of adverse growing conditions than are plants of 'Petite.' Plants of Spathiphyllum 'Claudia' grow taller than those of either 'Sparkle' or '31581'. The leaves of 'Claudia' are not so thick or leathery as those of both 'Sparkle' and '31581'. Plants of 'Claudia' grow to finished size more quickly than those of either parent.

The following observations, measurements and values describe plants grown in Zolfo Springs, Fla. at 10 months old (3 month old liner+7 months finish time), finished in 15 cm pots under greenhouse conditions which closely approximate those generally used in horticultural practice. All color references are measured against The Royal Horticultural Society (R.H.S.) Colour Chart. Colors are approximate as color depends on horticultural practices such as light level and fertilization rate, among other, without, however, any variance in genotype.

Classification:

*Commercial.*—*Spathiphyllum hybrid*cv. 'Claudia'.

Parentage:

*Female parent.*—Spathiphyllum 'Sparkle'.

*Male parent.*—Spathiphyllum '31581'.

Propagation: Vegetative, by tissue culture.

Plant: Under appropriate growing conditions, plant attains a size of approximately 48 cm to 55 cm in height from the top of the soil to the top of the leaf canopy and approximately 55 cm to 65 cm in width.

Leaves:

*Form.*—The leaf blade is ovate with an acuminate to acute apex and a cuneate base. The margins are entire and straight. The midrib is straight or slightly curved over the length of the leaf. The leaf blade is curved downward toward the leaf tip. The leaf surface is convex between the primary veins, giving the leaf a textured appearance. The leaf surface is shiny. The leaves of 'Claudia' are held approximately 40 degrees, or as much as 60 degrees from the vertical axis. This gives the plant an upright appearance.

*Size.*—Leaf blades are approximately 22 cm to 27 cm in length and approximately 8.8 cm to 10.9 cm in width.

*Petiole.*—The petiole is approximately 28 cm to 30 cm in length from the base of the petiole to the base of the leaf blade on the primary shoot. Secondary shoots are smaller depending on the age of the shoot. The petiole is approximately 4.5 mm in diameter just below the geniculum. There is one straight petiole below the geniculum.

*Petiole sheath.*—The petiole sheath is approximately 24 cm to 26 cm in length and approximately 1 cm in width at midpoint. The tip of the petiole sheath is rounded. There is approximately 1 cm to 1.5 cm between top of the petiole sheath and the base of the geniculum.

*Geniculum.*—The geniculum is approximately 3.0 cm in length, approximately 4.5 mm in diameter, and is straight or curved. The color is between RHS 146 B and RHS 146 C.

*Veins.*—Veins are sunken, and the leaf blade is convex between veins on the upper surface. The midrib is sunken. Well defined primary veins radiate out from the midrib over the length of the leaf. There are approximately 9–11 pairs of primary veins on the leaf.

*Color.*—Leaf: Upper Surface: Darker and greener than, but closest to RHS 139 A. Lower Surface: Darker than, but closest to RHS 147 B. Midrib: Upper Surface: Between RHS 137 A and RHS 137 B. Lower Surface: RHS 146 C. Petiole: RHS 147 B. Petiole sheath: Between RHS 147 B and RHS 147 C.

Roots: White fleshy roots with fine laterals.

Inflorescence:

*Immature.*—The spathe is tightly rolled around the spadix and emerges from the petiole sheath. The spathe is fully open approximately when the peduncle is fully elongated—approximately 50 cm–60 cm above the soil surface.

*Mature.*—Spathe: Size: The spathe is approximately 10 cm to 14 cm long and approximately 4.5 cm to 5.5 cm in width. It is cupped, and approximately 2.0 cm in depth. Color: Fully open: Adaxial surface: Whiter than, but closest to RHS 155 D. Abaxial surface: Whiter than, but closest to RHS 155 D. Midrib (adaxial): Lighter than, but closest to RHS 191 D. Midrib (abaxial): RHS 146 C. Apex: RHS 146 C (back); RHS 155 D tinged with RHS 146 D (front). Faded: Adaxial surface: RHS 146 C. Abaxial surface: Between RHS 146 B and RHS 146 C. Midrib: Upper surface: RHS 146 C. Lower surface: RHS 146 B. Apex: Between RHS 146 B and RHS 146 C (back); RHS 146 C tinged with RHS 146 B (front).

*Arrangement.*—The spathe terminates as a straight peduncle and opens vertically above the leaves. The peduncle is 146 B in color.

*Shape.*—The spathe is cupped, narrow and elliptic with an acute base and an accuminate apex which may be straight or twisted. Margins are smooth and entire.

*Flowering.*—Depending on season, approximately 3 to 6 blossoms will be present on plants. Smaller narrower blossoms may occur on less mature growth.

*Lastingness of individual inflorescence.*—Spathes of 'Claudia' begin to change from pure white to green after about 4 weeks, becoming almost entirely green after about 6 weeks. Cut flowers last about 7 days off the plant.

Reproductive organs:

*Spadix.*—Size: Approximately 2.4 cm to 4.1 cm in height and approximately 1.3 cm in width. Color: When the spathe unrolls, the spadix is RHS 158 C gradually changing to RHS 146 A. Stamens: Anthers and filaments are minute and not clearly visible. Pollen: RHS 155 D. Pistil: White in color, conical, protruding between the staminate flowers, firmly fixed to the main axil. The pistillate flowers extend approximately 2 mm beyond the staminate flowers. Seeds: Approximately 2 mm, reniform in shape, light to medium brown in color, with pitted seed coat texture. Each individual capsule contains approximately 1–5 seeds. Depending on size and degree of pollination, a single inflorescence can yield more than 250 seeds. Fruit: Oblong to elliptic berry, 6 mm long, 5–6 mm wide, green RHS 147 A becoming tinged with yellow RHS 19 A when ripe.

*Disease/pest resistance/susceptibility.*—Preventative disease and pest control measures used to grow crops of 'Claudia' are typical of ordinary common practice. 'Claudia' has no particular sensitivity to common pests or pathogens.

I claim:

1. A new and distinct cultivar of Spathiphyllum plant named 'Claudia,' as illustrated and described.

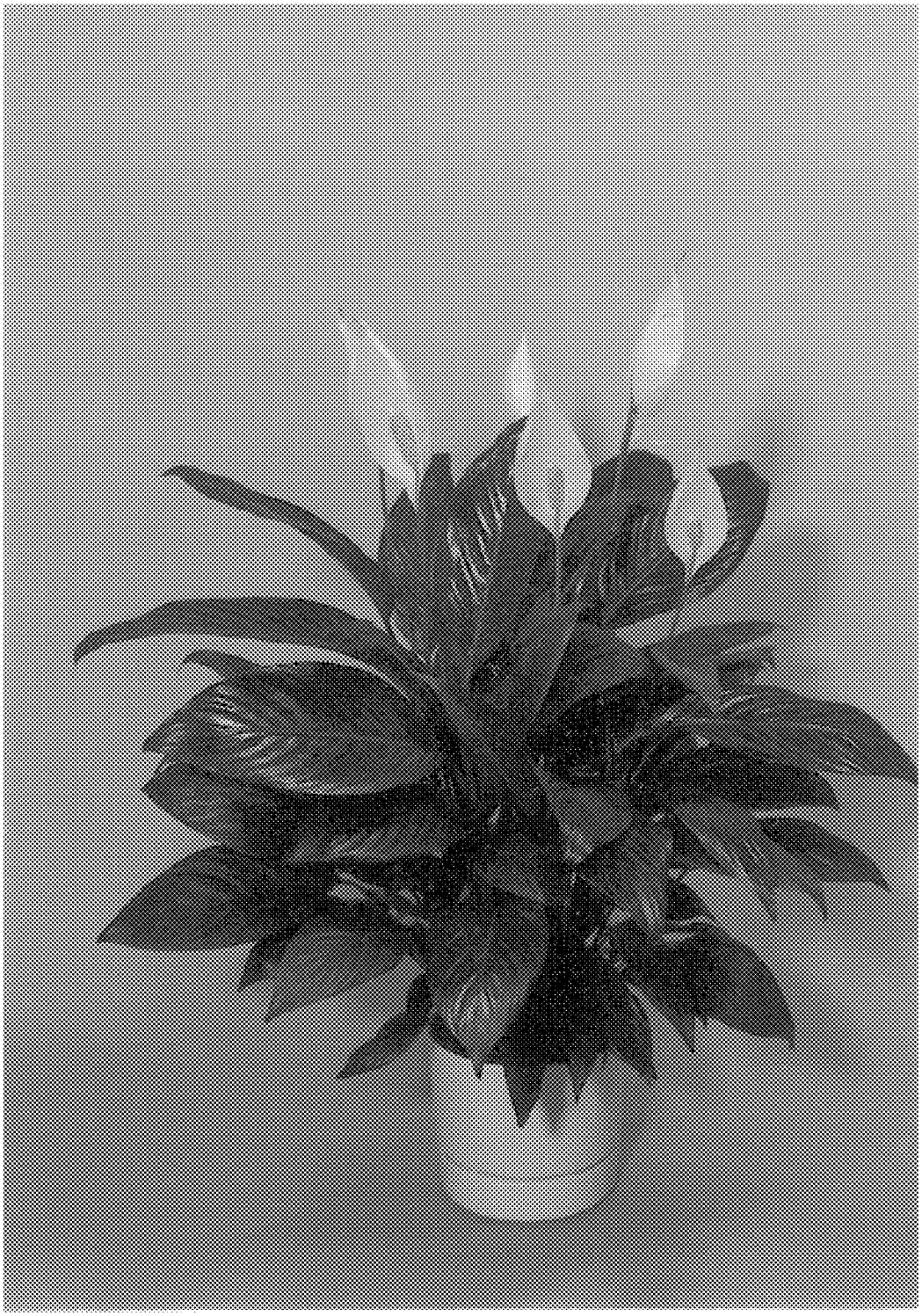

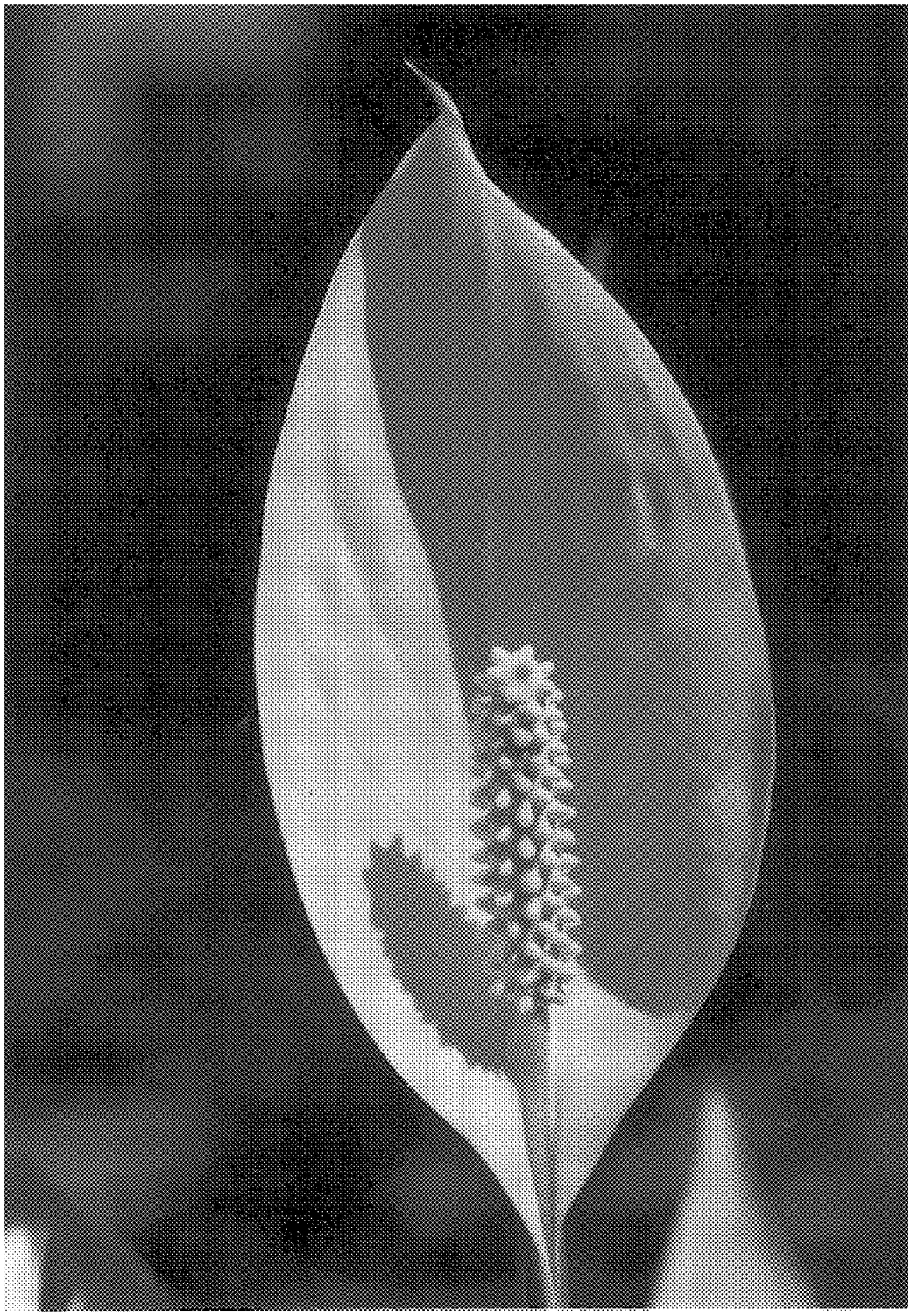

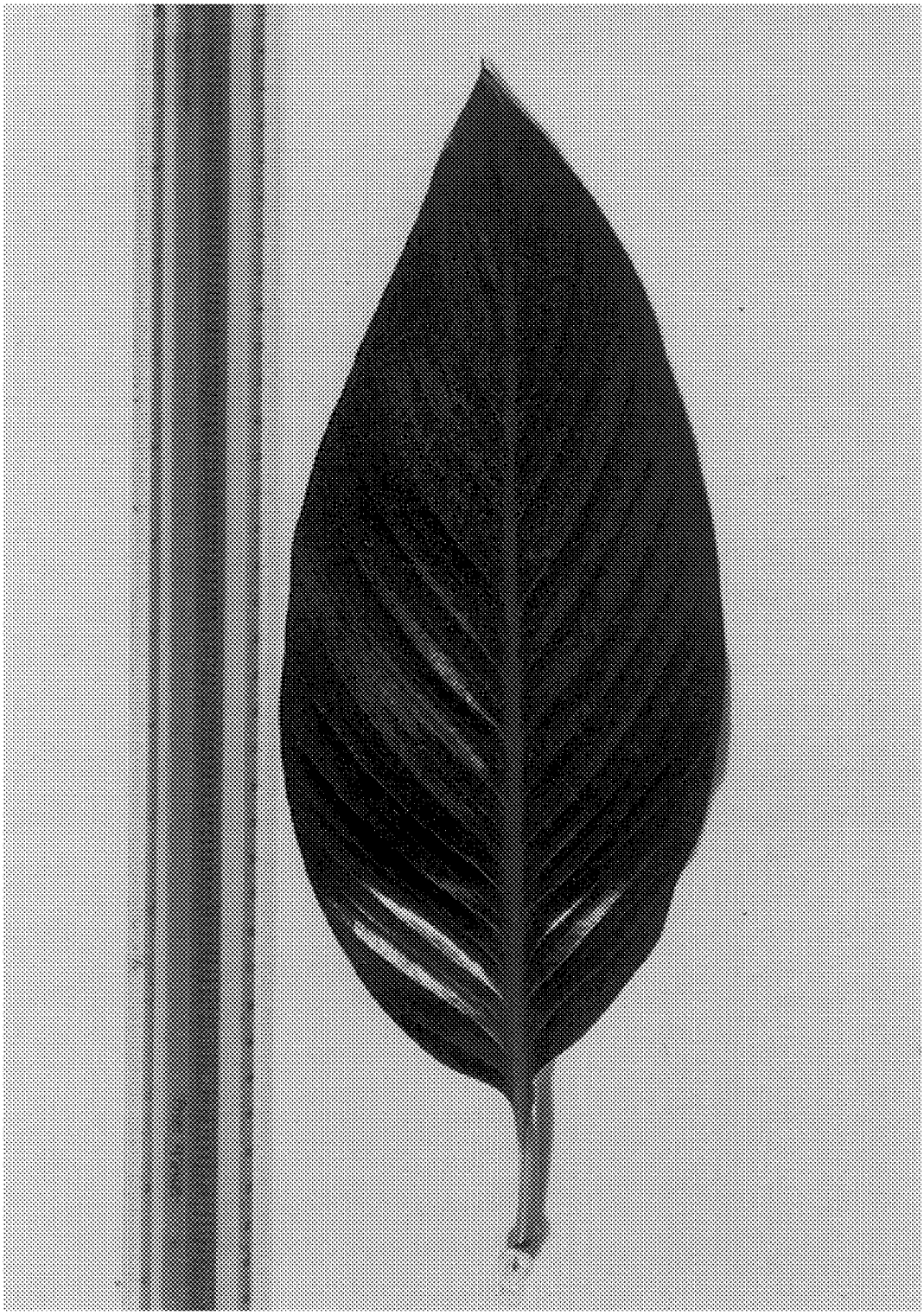

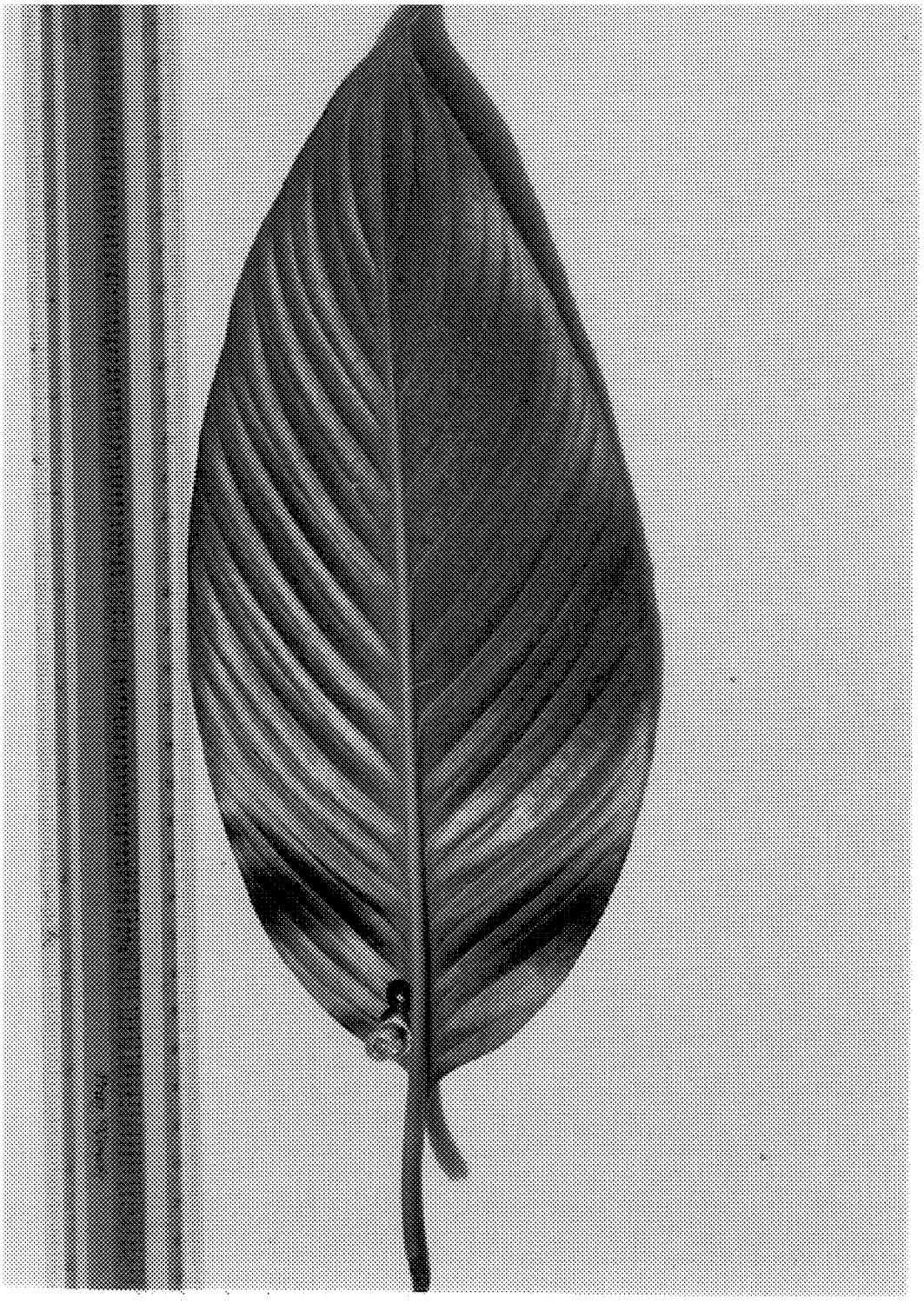

* * * * *